United States Patent [19]

Schintgen et al.

[11] Patent Number: 4,817,630

[45] Date of Patent: Apr. 4, 1989

[54] CONTROL CABLE FOR A BIOPSY FORCEPS

[76] Inventors: Jean-Marie Schintgen, 45, Avenue Victor Hugo, 75116 Paris; Bruno Zeitoun, 23, rue Daubenton, 75005 Paris, both of France

[21] Appl. No.: 115,415

[22] Filed: Nov. 2, 1987

Related U.S. Application Data

[62] Division of Ser. No. 870,238, Jun. 3, 1986, Pat. No. 4,721,116.

[30] Foreign Application Priority Data

Jun. 4, 1985 [FR] France .................................. 85 08387

[51] Int. Cl.$^4$ .............................................. A61B 10/00
[52] U.S. Cl. ...................................... 128/751; 128/772
[58] Field of Search ......................................... 128/4–8, 128/657, 749–758, 772; 604/95, 164, 170, 171

[56] References Cited

U.S. PATENT DOCUMENTS

| 2,118,631 | 6/1938 | Wappler | 604/170 |
|---|---|---|---|
| 3,552,384 | 1/1971 | Pierie | 604/95 |
| 3,840,003 | 10/1974 | Komiya | 128/751 |
| 3,964,468 | 6/1976 | Schulz | 128/751 |
| 4,178,810 | 12/1979 | Takahashi | 128/751 |
| 4,245,624 | 1/1981 | Kemiya | 128/772 |
| 4,646,751 | 3/1987 | Maslanka | 128/751 |
| 4,682,607 | 7/1987 | Vaillanwart et al. | 128/657 |

FOREIGN PATENT DOCUMENTS

| 67204 | 6/1969 | Fed. Rep. of Germany | 128/751 |
|---|---|---|---|
| 2926339 | 1/1980 | Fed. Rep. of Germany | 128/772 |
| 0233302 | 2/1986 | Fed. Rep. of Germany | 128/751 |
| 2505191 | 11/1982 | France | 128/772 |
| 194230 | 5/1967 | U.S.S.R. | 128/751 |

Primary Examiner—Max Hindenburg
Attorney, Agent, or Firm—Frishauf, Holtz, Goodman & Woodward

[57] ABSTRACT

A biopsy forceps has two cutting spoons or jaws articulated in a midportion at a common pivot which is fixed on a tubular extension at the end of a flexible control cable sheath. The ends of the jaws opposite their cutting ends are each articulated to link rods having their other ends articulated at a common pivot on the body of a needle which extends between the jaws to locate the place of taking a biopsy. The needle has a longitudinal slot which runs past the common pivot of the jaws, so that the needle is retracted as the jaws are closed by the needle body being drawn into the control cable end by a central control wire. An improved control cable sheath has its exterior ground to a smooth surface tampering down in diameter towards the end which carries the forceps. The central control wire may have its dimensional stability enhanced by wrapping it with a stainless steel coiled sheath, preferably wound in a direction opposite to the direction of winding the coiled stainless steel wire of the outer sheath of the control cable.

11 Claims, 2 Drawing Sheets

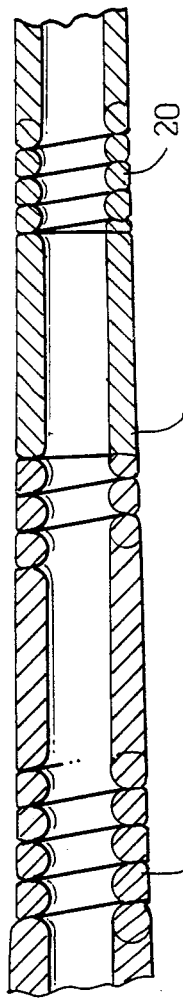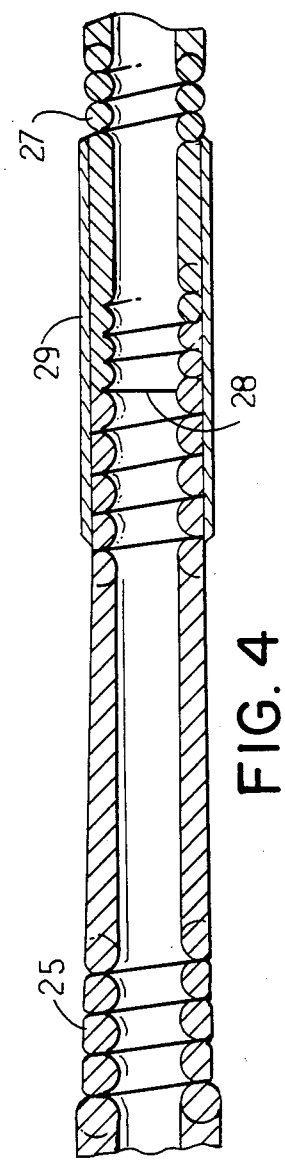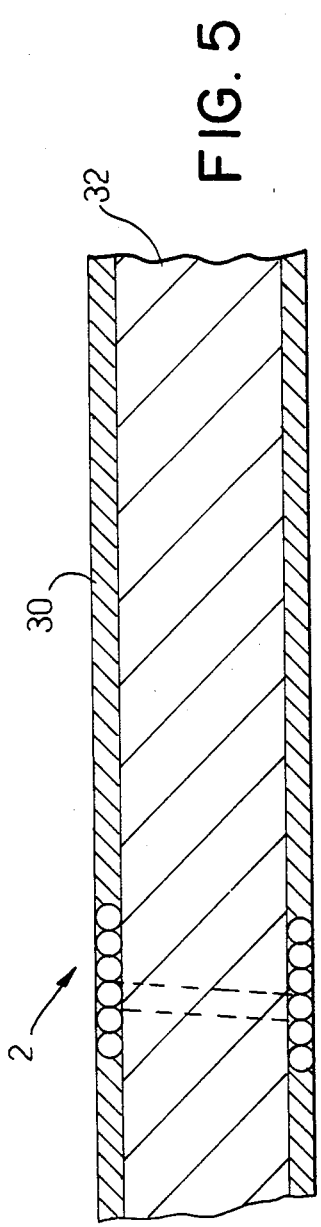
FIG. 3
FIG. 4
FIG. 5

CONTROL CABLE FOR A BIOPSY FORCEPS

This is a division of application Ser. No. 870,238 filed June 3, 1986, Pat. No. 4,721,116.

This invention concerns a biopsy forceps of the type comprising two spoons or jaws, each articulated on a pivoted link rod at one end of the sheath member of a mechanical control cable, the link rods being pivoted on a member fixed on the end of a central cable or wire running in the sheath and controlled by a handle or grip at the other end of the sheath member. A locating needle is mounted between the spoons or jaws. The control cable comprises a flexible sheath member formed of tightly coiled stainless steel wire within which the central wire or cable can be propelled lengthwise of the sheath member.

In the biopsy forceps of the above-mentioned type which are now known, the locating needle, which serves to determine the exact place for taking a body tissue sample, is mounted in fixed position between the two jaws, thus taking up some space which is lost for the biopsy.

Besides, in these known biopsy forceps, the jaws are articulated one on the other and their respective extremities opposite their cutting ends are each articulated on a link rod and the two link rods are themselves articulated on an actuating rod fixed on the adjacent extremity of the central control wire running within the sheath member. This usual disposition exhibits the inconvenience that the parallelogram formed by the two jaws and their control link rods articulated to the actuating rod at a single point can tilt around that point, which interfaces with the precision and effectiveness of taking the sample. Finally the putting together of this assembly having very small dimensions is a most delicate operation.

Moreover, in the known biopsy forceps the sheath member of the control cable is constituted basically of coiled stainless steel wire and, in order to provide increased flexibility at the distal end, certain known biopsy forceps have been provided with a sheath of smaller diameter connected to the main sheath member by a stainless steel piece, which requires two welds or brazed joints and gives rise to some interference with the longitudinal displacement of the sheath member, which needs to be displaced within the conduit of an endoscope. Furthermore, the external surface of the sheath member that needs to slide inside the endoscope tube is longitudinally rough and has circumferential (small pitch helical) ridges and grooves. This surface state that interferes with the sliding of the control cable sheath against the internal walls of the endoscope tube and gives rise to permature wearing down of the valves of the endoscope and additionally has the inconvenience of allowing the penetration of debris between the turns of the stainless steel wire.

In order to mitigate this inconvenience, certain biopsy forces have the control cable sheath covered on the exterior by a protective film, for example a PTFE film (a material available under the trademark Teflon). Even though this improves the sliding, the displacement of the sheath member is far from perfect in the course of the substantial deformations of the sheath member produced during its insertion, the protective film having a tendency to rupture and leaving the sheath member rough again and accessible to debris.

Finally, the central wire of the control cable is frequently not longitudinally stiff enough for firm cutting.

SUMMARY OF THE INVENTION

It is an object of the present invention to overcome the disadvantages of the known biopsy forceps as described above. More particularly it is an object of the invention to provide a novel forceps of simplified construction in which the needle is retracted in the course of closing the forceps and the jaws cannot pull out of position during the opening or the closing of the forceps. It is a further object of the invention to improve the facility of sliding the control cable sheath into position, preventing foreign matter from accumulating between the turns of the coiled-wire sheath and to improve both the sliding ability and the longitudinal dimensional stability of the central control wire.

Briefly, the link rods articulated at one end on the rear extensions of the jaws are pivoted at the other end on the needle body while the jaws are pivoted on a fixed axle or pivot on which a longitudinal aperture of the needle runs. This axle or pivot is fixed on a solid extension of the control cable sheath. Not only is the needle thereby retractable while closing the forceps, but the jaws cannot swing during closing and opening of the forceps.

In order to improve the lodgment of the needle in the mucus membrane during the closing of the forceps, the needle is preferably provided with laterally running notches, preferably of sawtooth profile.

As for the control cable, its sliding into position, within an endoscope or otherwise and the provision of flexibility at its distal end are facilitated by grinding the exterior of at least a part of the sheath including the distal end. Thus grinding the coiled stainless steel wire forming the sheath provides a smoother surface. Preferably the exterior diameter of the sheath is tapered down near the distal end to increase flexibility there. The central wire is given additional ease of sliding with a film of dry lubricant or with a coiled wire sheath welded thereto. The latter adds dimensional stability for quick, firm cutting.

Grinding is inexpensive and can be done industrially with precision, which is not the case with coating with a PTFE film. For special cases where extra flexibility is required at the distal end, two sheaths of different diameter can be joined end to end and ground to a continuous taper.

BRIEF DESCRIPTION OF THE DRAWINGS

The invention is further described by way of illustrative example with reference to the annexed drawing, in which:

FIG. 3 and FIG. 4 are sections respectively showing second and third preferred embodiments of tapered sheath members for a control cable for the forceps of FIG. 1, and FIG. 5 is a section of an improved form of central cable for running the control cable sheath.

DESCRIPTION OF THE ILLUSTRATED EMBODIMENTS

Figure 1:
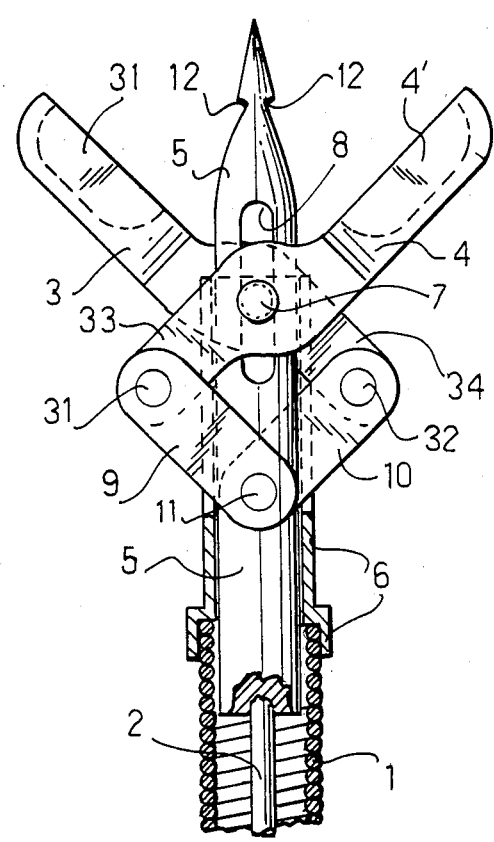
FIG. 1 is a schematic representation, partly in section, in a view parallel to the axis of the pivot of the jaws, showing a forceps according to the invention attached to the end of its control cable, omitting the remainder of the control cable.

The biopsy forceps illustrated in FIG. 1 has a control cable comprising a sheath member 1 within which a central actuating cable 2 is movable lengthwise. Only the end of the cable carrying the jaws is shown in the FIG. At the other end, not shown, is an actuating grip for moving the central cable within the sheath and thereby actuating the forceps.

The central cable 2 in moving lengthwise in the sheath member 1 under control of the actuating grip causes each of the two spoons or jaws 3, 4 to pivot on the other. The jaws respectively have cavities 3', 4'. The combined volume provided by the cavities 3' and 4' when the forceps constituted by the jaws 3 and 4 is closed makes up the volume of the sample that can be removed by the biopsy forceps. A needle member 5 serves to fix the position of the forceps for taking a biopsy.

In accordance with the invention, the central cable 2 is affixed to the rear extremity of the needle member 5 which is slidably mounted within a sleeve 6 which is fixed on the end of the sheath member 1 of the control cable, the jaws pivoting at the middle of their length on a rivet 7, fixed on the sleeve 6 and on which the slot 8 of the needle 5 runs. At their respective ends remote from the cavities 3', 4', the jaws 3 and 4 are respectively articulated on ends of link rods 9 and 10. The other ends of these link rods are articulated on a common axis or pivot 11 constituted by another rivet which in this case is fixed on the needle body 5.

The operation of the forceps is as follows. The lengthwise sliding displacement of the wire 2 draws the needle body 5 and the axle or pivot 11 which is in a fixed position thereon. The jaws 3 and 4 pivot about the fixed axle 7 along which the slot aperture 8 slides. By the traction of the wire 2, the forceps constituted by the jaws 3 and 4 closes while the needle body 5 disappears almost entirely in the space provided by the recesses 3', 4', so that the biopsy volume is maximal. The forceps 3, 4, guided at two points 7 and 11, cannot tip to one side or the other of the axis of the wire 2 and sleeve 6, as was the case with the previously known biopsy forceps.

Assembling the forceps that has just been described is easier and quicker than that of the previously known biopsy forceps. Besides, in comparison with a biopsy forceps of a known needle-equipped type, the forceps according to the invention in which the needle and the actuating rod propelled by the end of the central control wire are made integral, has one less piece-part, resulting in economy in the manufacturing operations of drilling, crimping and assembly. The biopsy forceps according to the invention is therefore less expensive to make than the previously known biopsy forceps.

In accordance with a preferred embodiment of the invention the point of the needle body 5 is equipped with laterally running notches 12. During withdrawal of the needle 5 which brings about the closing of the forceps 3, 4 and the penetration of the cutting edges of the jaws into mucous tissue for performing the biopsy, there notches 12 oppose withdrawal of the needle 5 from the mucous membrane, which favors the setting of the forceps in the mucus and improves the taking of the sample, particularly in the case of resistant mucus tissue.

Figure 2:
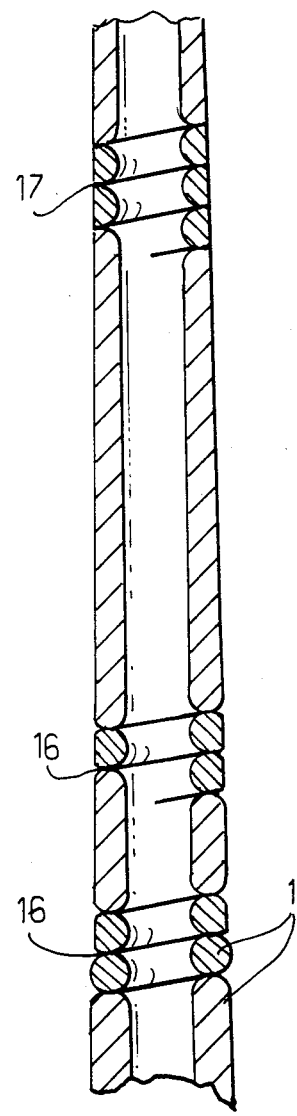
FIG. 2 is a longitudinal section of the end portion of the outer sheath of a first preferred embodiment of control cable for the forceps of FIG. 1.

FIG. 2 shows a cross section of the end portion of a control cable in an embodiment in which the external surface of the sheath member 2 is ground down to remove roughness of the outside of the longitudinal tight wire coil that constitutes the sheath. The smooth external surface, in addition to having a good appearance, has the advantage of assuring easy advance of the control cable sheath within the guide tube of an endoscope and also avoiding the trapping of debris between the turns of the stainless steel wire. These advantages last for the service life of the control cable.

In the case illustrated in FIG. 2, the entire length of the sheath is not ground to produce a smooth exterior, but only a portion beginning at 15 and continuing to near the distal end (not shown) which carries the forceps. Furthermore, the grinding of the outer surface of the sheath 2 is such as to taper down the outer diameter of the sheath towards the end of the control cable. FIG. 2 shows that at 16, not far from where the grinding of the sheath begins, grooves are still visible between adjacent turns of the stainless steel wire which is tightly coiled to make the sheath.

Where the grinding down of the outer surface removes half or nearly half of the thickness of the wire, the outer surface is smooth as shown at 17. At the same time that the exterior surface becomes progressively smoother and the external diameter slightly smaller, the flexibility of the sheath increases because of the reduced amount of metal in each of the turns of the coiled wire. Beyond the location 17 of FIG. 2, continuing to the distal end of the sheath the grinding smooth of the sheath produces a constant outer diameter. To simplify the drawing, the actual cross section of the sheath is not shown between the locations 15, 16 and 17 and it is to be understood that the cross section indicated symbolically with wide cross hatching in FIG. 2 continues with sections intermediate between those shown at 16 and 17 between those locations, and so on. The central control wire 2 is omitted in FIG. 2 in order to simplify the drawing.

FIG. 3 is a cross section similar to FIG. 2 of a structure that permits a greater taper of the sheath and thus a greater increase of flexibility towards the end of the cable. In this case, a tubular liaison piece is used to connect a taper-ground sheath portion 19 to another sheath portion 20 of smaller diameter of the wire coil, likewise ground smooth, but ground to a uniform diameter. The sheath portion 20 has the higher flexibility desired near the distal end of the sheath.

FIG. 4 shows another way of joining sheaths of wire of different sizes, in this case fitting the sheath 25 formed by coiling a heavier wire to the sheath 27 formed by coiling a smaller wire, the coils abutting at the interface 28. The sleeve 29 is brazed on over the abutting ends of the two coiled wire sheaths.

The sleeve 30 in FIG. 4 covers untapered ground ends of the two sheath sections 25 and 27 and is itself of constant diameter. Since it is thin it produces only small resistance to advance or retraction of the biopsy forceps in an endoscope channel.

The connecting sleeve 18 (liaison piece) of FIG. 3 can advantageously be tapered even when the smaller sheath 20 connected to it, although ground smooth, is not tapered. It may be desirable for the more flexible section of sheath between the connecting sleeve and the distal end to have flexibility that no longer increases towards the end where the forceps are attached.

FIG. 5 shows an improved construction of the central control wire 2. In order to prevent the wire from buckling or, if it is a stranded control wire, from becoming compressed and extended lengthwise when pushed or pulled, an internal coiled wire sheath 30 of stainless steel wire is wound around a central wire 32. Preferably, the coiled wire sheath 30 is wound in the direction opposite to the direction of winding the wire that constitutes the outer sheath 1 (FIGS. 1 and 2). Furthermore, to facilitate the advance and retraction of the central control wire 2, a self-lubricating solid film, such as a PTFE film (polytetrafluoroethylene) is applied to the outer surface of the control wire 2, preferably by being welded on after being mounted thereon, as shown in FIG. 4 where the sheath 30 is welded on the outside of the central control wire 32.

With a central control wire in accordance with FIG. 4, there is no lost motion when the forceps jaws 3 and 4 begin to bit into resistant tissue, because the central wire maintains stable position and dimension and makes possible firm and neat cutting which is done quickly.

Although the invention has been described with reference to particular illustrative embodiments, it will be recognized that modifications and variations are possible within the inventive concept.

We claim:

1. Control cable for a surgical cutting forceps comprising a control wire for attachment to a cylindrical plug slidably held in a tube for moving two pivoting jaws pivoted on a first end of said tube and a flexible tubular sheath of circular cross-section surrounding said control wire over the full length of the sheath, made of stainless steel helicoidal wire with adjacent turns uniformly wound tightly over its length and attachable at its distal end to said tube, wherein the external surface of at least a part of the sheath, including a distal end portion thereof, is reduced in outer diameter by grinding into a shape which is longitudinally flattened and circumferentially symmetrical with respect to centers of the cross-sections of the sheath in the part of the sheath having a reduced outer diameter, at least part of said reduced diameter portion having a shape gradually tapering down in girth towards said distal end.

2. Control cable according to claim 1, wherein said sheath is made of at least two helicoidal wire sections assembled together by means of at least one liaison piece.

3. Control cable according to claim 2, wherein said control wire is coated with a film of self-lubricating material.

4. Control cable according to claim 3, wherein said self-lubricating material includes polytetrafluoroethylene.

5. Control cable according to claim 1, wherein said control wire is coated with a film of self-lubricating material.

6. Control cable according to claim 5, wherein said self-lubricating material includes polytetrafluoroethylene.

7. Control cable according to claim 1, wherein said control wire is fixed inside a second sheath of helicoidal wire inside said sheath attachable to said tube, said second sheath closely covering said control wire.

8. Control cable according to claim 7, wherein the direction of winding of said second sheath is opposite of that of said sheath inside of which said second sheath said control wire is located.

9. Control cable according to claim 1, wherein between said distal end and said part of said sheath which is of reduced diameter and of tapered shape said distal end portion of said sheath is of constant diameter and of smooth external surface.

10. Control cable according to claim 9, wherein said constant diameter portion of said part of said sheath which is of reduced diameter is made of a wire coil of smaller diameter than the helicoidal wire forming the remainder of said sheath and is joined to said remainder of said sheath by a tubular laison piece.

11. Control cable according to claim 9, wherein said constant diameter portion of said part of said sheath which is of reduced diameter is made of a wire coil of smaller diameter than the helicoidal wire forming the remainder of said sheath and is joined to said remainder of said sheath by a sleeve brazed on over abutting ends of the respective distal end and remainder sheath portions.

* * * * *